(12) United States Patent
Gorman et al.

(10) Patent No.: US 6,935,187 B1
(45) Date of Patent: Aug. 30, 2005

(54) TEST METHOD FOR ASSESSING THERMAL MECHANICAL FATIGUE PERFORMANCE OF A TEST MATERIAL

(75) Inventors: Mark Daniel Gorman, West Chester, OH (US); Shesh Krishna Srivatsa, Cincinnati, OH (US); Philemon Kennard Wright, III, Wyoming, OH (US); Christine Govern, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/792,158

(22) Filed: Mar. 3, 2004

(51) Int. Cl.[7] .............................................. G01N 3/32
(52) U.S. Cl. ...................................................... 73/811
(58) Field of Search ........................... 73/811, 787, 808

(56) References Cited

U.S. PATENT DOCUMENTS

| | | | |
|---|---|---|---|
| 3,795,134 A * | 3/1974 | Eichenbrenner et al. ...... 73/797 |
| 4,748,854 A | 6/1988 | Rao |
| 4,933,239 A * | 6/1990 | Olson et al. ................. 428/557 |
| 5,967,660 A | 10/1999 | Akpan et al. |
| 5,980,103 A * | 11/1999 | Ikuno et al. ................ 73/865.6 |
| 5,980,206 A * | 11/1999 | Hunter et al. ........... 416/134 A |
| 6,595,068 B2 | 7/2003 | Brovold et al. |
| 6,761,073 B2 * | 7/2004 | Otobe et al. .................. 73/766 |

* cited by examiner

Primary Examiner—Max Noori
(74) Attorney, Agent, or Firm—McNees Wallace & Nurick LLC

(57) ABSTRACT

A test method for testing the thermal mechanical fatigue performance of a test material includes preparing a test specimen of the test material, wherein the test specimen has a base, and a rib extending outwardly from the base. The test specimen is thermally cycled through at least one test cycle. In each test cycle the rib is heated to a higher rib temperature and thereafter cooled to a lower rib temperature. The test specimen is evaluated for thermal mechanical fatigue damage.

25 Claims, 3 Drawing Sheets

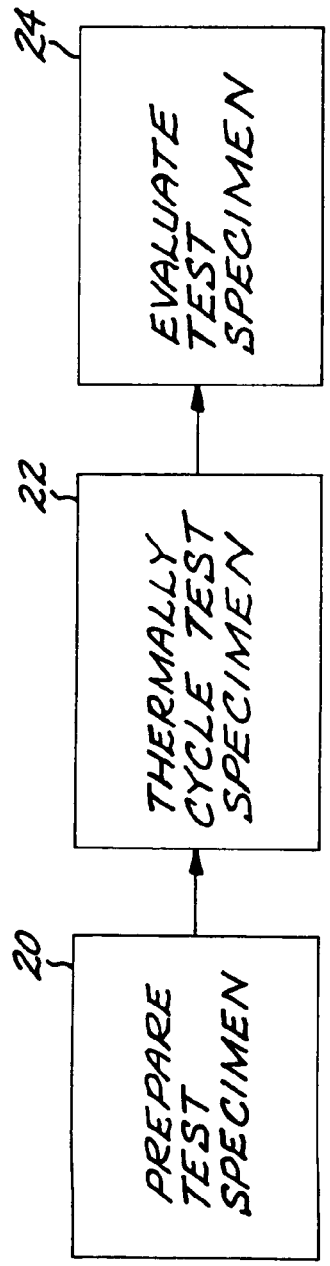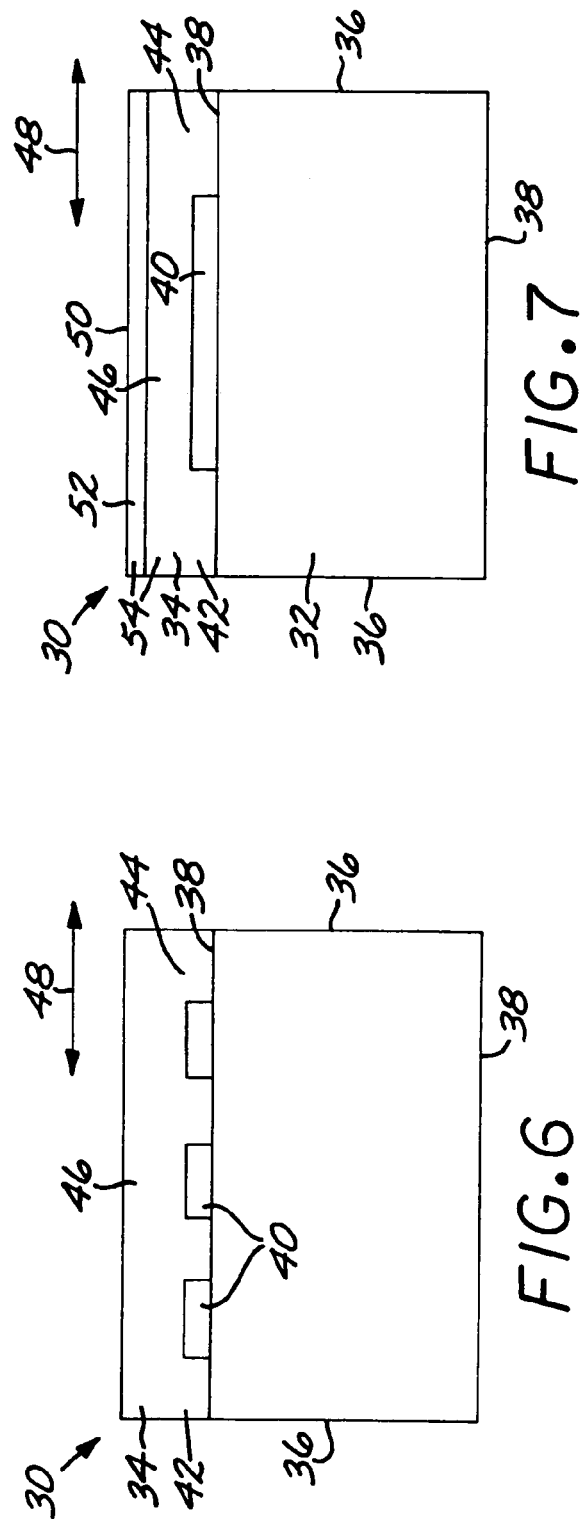

TEST METHOD FOR ASSESSING THERMAL MECHANICAL FATIGUE PERFORMANCE OF A TEST MATERIAL

This invention relates to the testing of materials and, more particularly, to evaluating the thermal mechanical fatigue performance of materials used in aircraft gas turbine engines.

BACKGROUND OF THE INVENTION

In an aircraft gas turbine (jet) engine, air is drawn into the front of the engine, compressed by a shaft-mounted compressor, and mixed with fuel. The mixture is combusted, and the resulting hot combustion gases are passed through a turbine mounted on the same shaft. The flow of gas turns the turbine by contacting an airfoil portion of the turbine blade, which turns the shaft and provides power to the compressor. The hot exhaust gases flow from the back of the engine, driving it and the aircraft forward. There may additionally be a bypass fan that forces air around the center core of the engine, driven by a shaft extending from the turbine section.

In service, the components of the turbine section of the engine are repeatedly thermally cycled between lower and higher temperatures. The thermal cycles may be between room temperature and the operating temperature when the engine is started, operated, and shut down, or between an intermediate temperature and a higher operating temperature when the engine power output is changed between lower and higher power settings. Some of the components are mechanically loaded during the thermal cycling.

One of the components that is subjected to the greatest temperature extremes and the greatest mechanical loadings during thermal cycling is the turbine blade. The turbine blade has a complex shape, including an attachment section, an airfoil with a thin tip portion, and a platform. The airfoil is in the direct flow of the hot combustion gases. The turbine blade is typically made of an alloy that has good high temperature mechanical properties.

As a result of its material of construction and the nature of its thermal and mechanical loadings during service, the turbine blade, particularly the airfoil and airfoil tip, are subject to thermo mechanical fatigue (TMF). The combination of thermally induced stresses, mechanically induced stresses, and the temperature extremes can combine to cause the formation and propagation of cracks in the airfoil of the turbine blade, particularly in its airfoil tip, that lead to premature failure of the turbine blade. Because the turbine blade rotates at up to 20,000 rpm, such a premature failure may lead to an unplanned removal from service or major damage of the engine.

It is therefore important to evaluate the performance of the turbine blade with regard to its material of construction and the loading conditions to ensure that the turbine blade can withstand the thermal mechanical fatigue and will not fail prematurely. There are a variety of testing procedures used, including full scale tests of the turbine blades, tests of proxy specimens such as cylindrical test bars which are used in the hope that their performance will reflect the performance of the turbine blades, and accelerated tests using special test equipment. All of the available testing approaches have shortcomings. The full-scale tests are expensive, the tests of proxy specimens do not necessarily reflect the performance of the turbine blade, and accelerated tests are not a good indicators of actual service performance and do not permit a realistic evaluation of the materials and conditions. Stresses imposed in other simulative tests fail to accurately account for the complex effects of the test material in determining the stress that results due to a number of factors such as thermal expansion coefficient, elastic modulus, emissivity, thermal conductivity, and yield strength, all of which vary with temperature.

There remains a need for an improved approach to evaluating components of gas turbine engines, as well as articles subjected to similar conditions, to evaluate their thermal mechanical fatigue performance. The present invention fulfills this need, and further provides related advantages.

SUMMARY OF THE INVENTION

The present invention provides a technique for evaluating the thermal mechanical fatigue performance of materials and articles that are used in conditions of temperature variations and mechanical loading. This approach particularly provides a good indicator of the thermal mechanical fatigue performance of materials such as nickel-base superalloys that form turbine blades. The present approach is simple and inexpensive to implement.

The test method for testing the thermal mechanical fatigue performance of a test material comprises the steps of preparing a test specimen of the test material, wherein the test specimen comprises a base, and one or more ribs extending outwardly from the base, and thermally cycling the test specimen through at least one test cycle, and preferably to a plurality of test cycles. In each test cycle the rib is heated to a higher rib temperature and thereafter cooled to a lower rib temperature. ("Higher" and "lower" are used relative to each other in this context, and do not denote any specific temperatures.) The rib may be held at the higher rib temperature for a period of time before cooling. The test cycle may be complex, with several stages of heating, cooling, and holding at temperature. In the thermal cycling, the test specimen may be heated generally, or only the rib may be heated locally. The test specimen, and particularly the rib, is evaluated for thermal mechanical fatigue damage, such as the presence of fatigue cracks. With this type of evaluation, no instrumentation of the test specimen is required during the thermal cycling.

The test material may be of any operable type, but is typically a nickel-base superalloy test material. Such nickel-base superalloys are used in most turbine blades for aircraft gas turbine engines. The present approach allows such test materials to be evaluated and comparatively tested before going to the expense of fabricating the actual gas turbine components for testing. The present approach may also be used to evaluate the effects of different thermal and mechanical loading cycles.

The rib of the test specimen may be solid. There may instead be one or more slots through the rib and extending parallel to the long direction of the rib. In the slotted configuration of a single slot, the rib is supported from the base at a first end of the rib and at a second end of the rib, but does not contact the base in a central portion of the rib. Where there is more than one slot, the rib is supported from its ends and also from intermediate locations along its length. The slots may be of the same lengths or of different lengths. The rib may have hollow cavities therein. The rib may be coated with protective coatings or may be made of an alternate material.

The base must have a relatively large size and mass as compared with the rib, in order to properly constrain the expansion and contraction of the rib. In one embodiment, a mass of the base is at least 25 times larger than a mass of the rib. Desirably, the test specimen has a width of the base at least 5 times larger than a width of the rib, and/or a height of the base at least 3 times larger than a height of the rib.

The rib should be maintained in compression while the rib is heated toward the higher rib temperature during the heating part of the cycle. However, the rib may go into tension if the rib compressively yields or creeps. Likewise, the rib goes into tension during cooling. This stress state is achieved by having the average rib temperature higher than the average base temperature during heating and lower during cooling, and by having the base sufficiently stiff to resisting bending loads imposed by the ribs. At least a portion of the base may be insulated, such as by packing it in insulation, to aid the thermal control and to ensure that the rib is in compression at the higher rib temperature.

Analysis of the heat flow of the test specimen during the test cycle, as well as preliminary test results, indicates that the present approach produces a good indicator of the susceptibility of the material to thermal mechanical fatigue.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIG. 1 is a block diagram of a method in accordance with an embodiment of the invention;

FIG. 6 is a side view of a third embodiment of the test specimen;

FIG. 7 is a side view of a fourth embodiment of the test specimen;

DETAILED DESCRIPTION OF THE INVENTION

FIG. 1 depicts an embodiment of a test method for testing the thermal mechanical fatigue performance of a test material. The test method first includes preparing a test specimen 30 of the test material, step 20. The test material is preferably a nickel-base superalloy. As used herein, "nickel-base" means that the composition has more nickel present than any other element. The nickel-base superalloys are typically of a composition that is strengthened by the precipitation of gamma-prime phase or a related phase. The test material may instead be other metallic materials, a ceramic, or a combination of materials.

Figure 3:
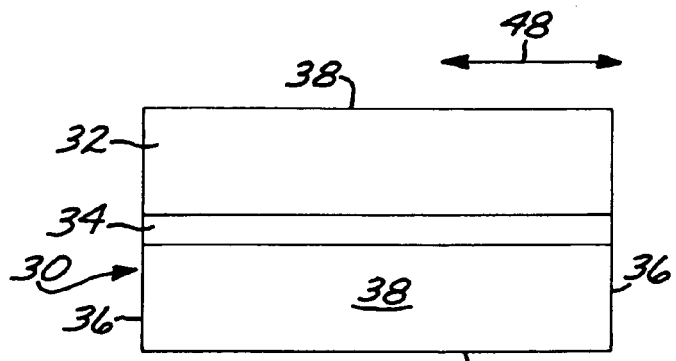
FIGS. 2–4 are a set of elevational views of a first embodiment of a test specimen, with FIG. 2 a side view, FIG. 3 a top view, and FIG. 4 an end view.
Figure 4:
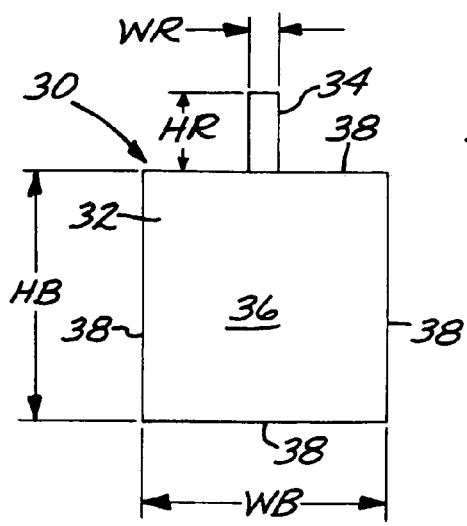
Figure 2:
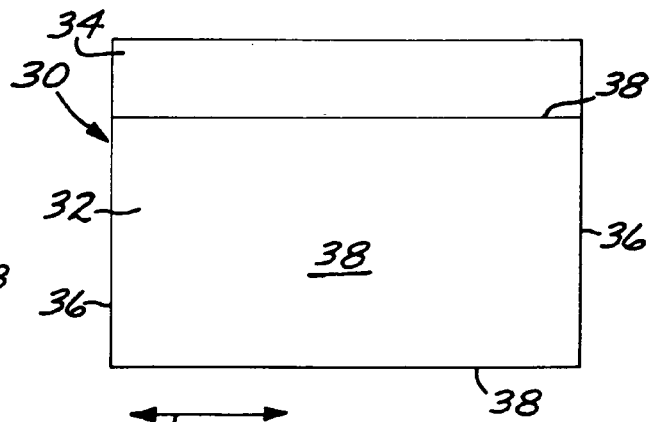

FIGS. 2–4 illustrate an embodiment of the test specimen 30. The test specimen 30 comprises a base 32, and at least one rib 34 extending outwardly from the base 32. As illustrated, the base 32 is a rectangular prism with two parallel ends 36 and four lateral faces 38. The rib 34 extends outwardly from one of the lateral faces 38.

The base 32 must have a much larger mass than the rib 34. Preferably, the test specimen 30 has a mass of the base 32 at least 25 times larger than a mass of the rib 34. In one design, a width WB of the base 32 is at least 5 (and often more) times larger than a width WR of the rib 34. In another embodiment, a height HB of the base 32 is at least 3 (and often more) times larger than a height HR of the rib 34. The combination of heights and widths is selected so that the mass ratio is at least 25.

Figure 5:
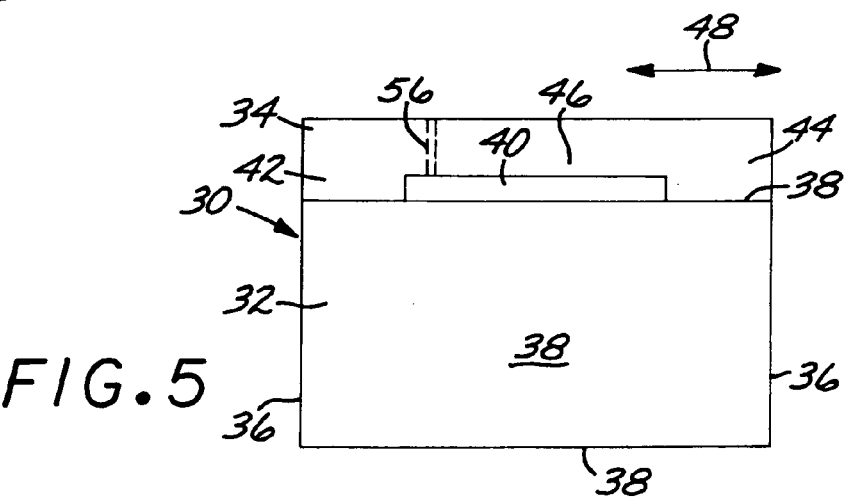
FIG. 5 is a side view of a second embodiment of the test specimen.
Figure 8:
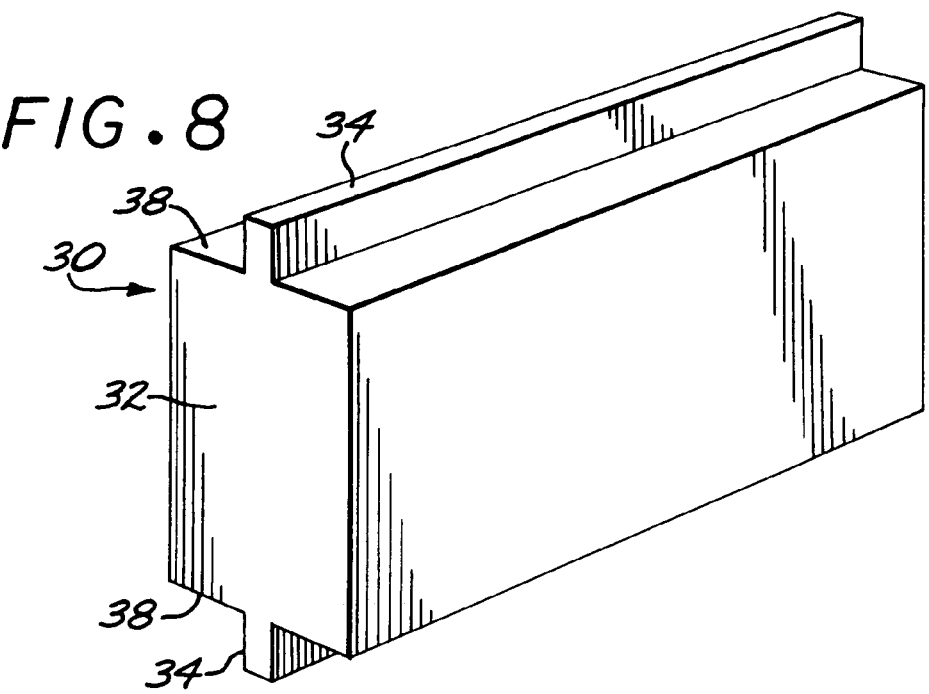
FIG. 8 is a perspective view of a fifth embodiment of the test specimen.

FIGS. 5–8 depict other embodiments of the test specimen 30. The embodiments are similar to that of FIGS. 2–4, whose discussion is incorporated as appropriate, except as noted next. In the embodiment of FIG. 5, there is a slot 40 through the rib 34, extending parallel to a lengthwise direction 48 of the rib 34. That is, the rib 34 is supported from the base 32 at a first end 42 of the rib 34 and at a second end 44 of the rib 34. The rib 34 does not contact the base 32 in a central portion 46 of the rib 34. The central portion 46 of the rib 34 is thereby thermally isolated from the base 32. The embodiment of FIG. 6 is similar to that of FIG. 5, except that there are multiple (i.e., two or more) slots 40 in the rib 34. The rib 34 is thereby supported from the base 32 at the ends 42 and 44 of the rib 34, and also at one or more additional locations along the length of the rib 34. The multiple slots 40 may be of the same length, as illustrated, or of different lengths to provide a range of sensitivities. In the embodiment of FIG. 7, a top 50 of the rib 34 comprises a strip 52 of a strip material joined to the remainder of the rib 34, extending parallel to the lengthwise direction 48. The joint of the strip 52 to the remainder of the rib 34 may be a weld, a diffusion bond, a mechanical joint, or other type of joint. The strip material that forms the strip 52 may be the same material as the rib material that forms the remainder of the rib 34, or a different material. The approach of FIG. 7 is particularly useful in testing the performance of weldments or other types of attachments at the tip of a turbine blade. The embodiment of FIG. 7 having the strip 52 is illustrated in relation to the single-slot embodiment otherwise shown in FIG. 5, but it may be used in relation to the multiple-slot embodiment of FIG. 6, the unslotted embodiment of FIGS. 2–4, or other operable embodiment. The embodiment of FIG. 8 has two ribs 34 on opposing faces 38 of the base 32. Any of the compatible features discussed in relation to the other embodiments may be used with the embodiment of FIG. 8.

In these embodiments of FIGS. 2–8, the test specimen 30 is illustrated as rectilinear in its general shape. It may instead have other shapes, such as a cylinder or a disk.

The rib 34 may be coated with a coating 54 such as a protective coating so that the performance of the coating on the test specimen may be evaluated. The coating may be, for example, an environmental coating (e.g., an aluminide or platinum aluminide coating) or a thermal barrier coating (e.g., a bond coat with an overlying ceramic thermal barrier). The presence of the protective coating 54 is illustrated in FIG. 7, but it may be used in relation to the embodiments of FIGS. 2–6 and 8 as well.

The rib 34 may include hollow cavities 56 therein, to simulate internal cooling passages. The presence of a hollow cavity 56 is illustrated in FIG. 5, but it may be used in relation to the embodiments of FIGS. 2–4 and 6–8 as well.

Figure 9:
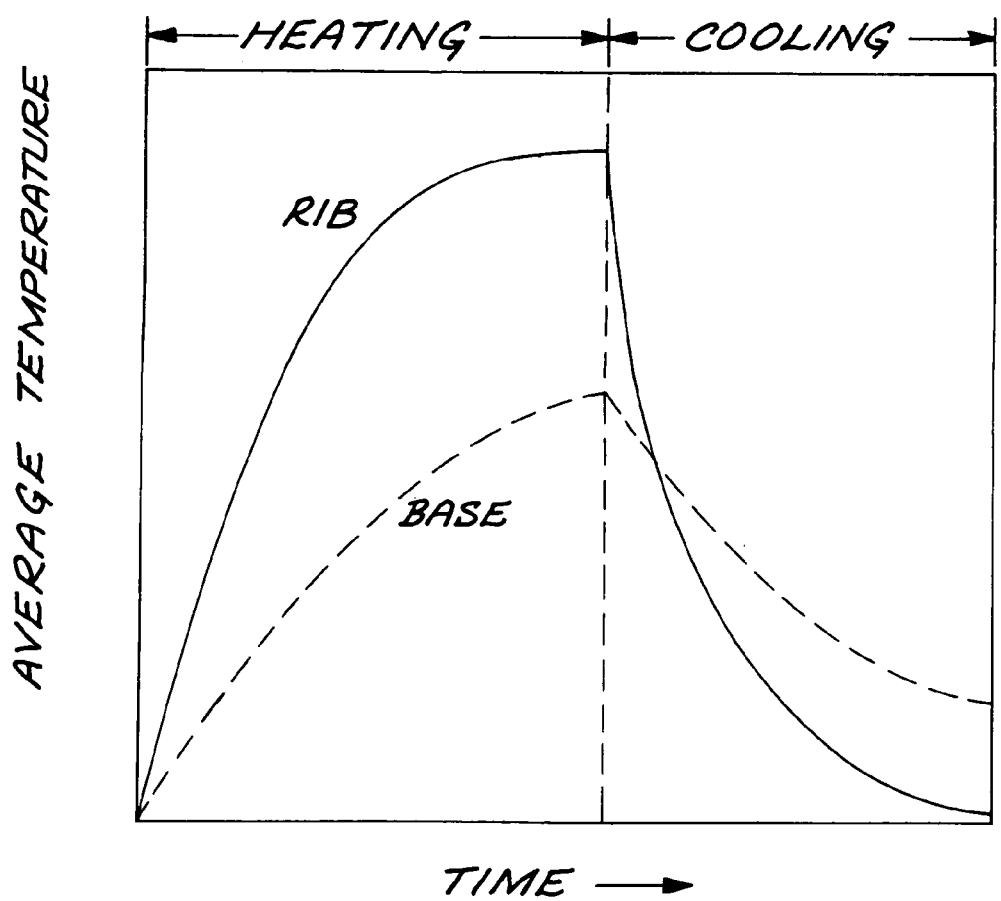
FIG. 9 is a graph of temperature versus time for the rib and the base during heating and cooling.

Returning to the discussion of FIG. 1, the test specimen 30 is thermally cycled through at least one test cycle, and typically a plurality of test cycles, step 22. In each test cycle, the test specimen 30 is heated to a higher rib temperature and thereafter cooled to a lower rib temperature. The test specimen 30 may also be held at the higher rib temperature and/or at the lower rib temperature for a period of time. FIG. 9 depicts the average temperature of the rib 34 and the base 32 during a typical test cycle including heating and cooling. Because of its smaller dimensions and thermal mass, and relatively larger surface area, the average temperature of the rib 34 leads that of the base 32. That is, the rib 34 reaches the higher temperatures faster than does the base 32 during heating. During cooling, the rib 34 is initially at a higher temperature than the base 32, and then falls to the lower temperature faster than does the base 32 during the latter portion of the cooling period. The result is that the rib 34 is in compression at the higher temperatures, the desired stress state. Insulating the base 32 accentuates this temperature-difference behavior of the rib 34 relative to the base 32.

The test cycles may be simple in their form of temperature as a function of time, with a heating and cooling, and optional hold period. The test cycles may instead be more complex in their temperature-time form, with several patterns of heating, cooling, and intermediate holds during the heating or cooling. There is no limitation on the types of cycles that may be used in step 22. The heating and cooling may be accomplished generally, with the entire test specimen 30 heated and cooled as a single piece, or heating and cooling may be accomplished locally, as by preferentially heating and cooling the rib 34. One virtue of the present approach is that there is no use of complex, expensive force-applying machinery or the like that would constrain the selection of the form of the temperature-time test cycle, or with the selection of the mode of heating and cooling. Another virtue is that the test approach naturally accounts for the temperature-dependent effects of the material on the induced stress. Desirably, the rib 34 is maintained in compression while the rib 34 is heated toward the higher rib temperature and is at the higher rib temperature. This result may be achieved by maintaining the base 32 at a lower temperature than the rib 34 when the rib is at the higher rib temperature. The base 32 may be packed in an insulation, such as a fiber or foam ceramic insulation, to further aid in controlling the rates of heat input into and heat removal from the base 32.

The test specimen is evaluated, step 24, for thermal mechanical fatigue damage. The evaluation 24 may be of any type. For example, the test specimen may be evaluated optically for the presence of fatigue cracks in the rib 34. The evaluation 24 may be performed either after step 22 is complete, or at an intermediate stage of the test cycling of step 22.

The present approach has been reduced to practice, both with thermal analysis of the operability of the test specimen 30 and with actual testing.

Thermal and stress analysis using computer modeling was employed to design the geometry of the test specimen and the nature of the thermal cycle to which it should be thermally cycled in order to duplicate the temperature and strain cycle of the tip of a turbine blade. This modeling ensures that the results for the test specimen simulates the turbine blade tip thermal fatigue cracking. The simulation included modeling the heatup of the test specimen in the heatup furnace subject to the appropriate thermal boundary conditions. In the model, the furnace and the test specimen were brought up to a specified temperature, held at that temperature, and cooled. The base was insulated on all of the four vertical faces. The faces were exposed to the furnace ambient temperature. During heating, the rib was heated by radiation and convection from the furnace. Subsequent to heatup and hold, the cooling of the test specimen was modeled. During cooling, the rib cooled by radiation and convection to air. The temperature predictions were validated with measured thermocouple data. Stress analysis was performed by modeling the test specimen using a three-dimensional thermal-elastic-plastic analysis. The thermal exposure of the specimen caused thermal strains in the specimen and the resulting stress-strain behavior was computed using coupled thermal-stress analysis.

A test sample according to the present design of Rene N5 nickel-base superalloy was prepared according to the present approach and tested by cycling an air furnace set at 2450° F. and room temperature. Thermal-fatigue failure was observed after 48 cycles when a 0.500 inch slot was used, and after 142 cycles when a 0.250 inch slot was used.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A test method for testing the thermal mechanical fatigue performance of a test material, the test method comprising the steps of:
preparing a test specimen of the test material, wherein the test specimen comprises
a base, and
a rib extending outwardly from the base;
thermally cycling the test specimen through at least one test cycle, wherein in each test cycle the rib is heated to a higher rib temperature and thereafter cooled to a lower rib temperature; and
evaluating the test specimen for thermal mechanical fatigue damage.

2. The test method of claim 1, wherein the step of preparing includes the step of
preparing the test specimen of a nickel-base superalloy test material.

3. The test method of claim 1, wherein the step of preparing includes the step of
preparing the test specimen with two ribs extending outwardly from the base.

4. The test method of claim 1, wherein the step of preparing includes the step of
preparing the test specimen with at least one slot in the rib, wherein each slot extends parallel to a lengthwise direction of the rib.

5. The test method of claim 1, wherein the step of preparing includes the step of
preparing the test specimen with exactly one slot in the rib extending parallel to a lengthwise direction of the rib, so that the rib is supported from the base at a first end of the rib and at a second end of the rib, but does not contact the base in a central portion of the rib.

6. The test method of claim 1, wherein the step of preparing includes the step of
preparing the test specimen with more than one slot in the rib, wherein each slot extends parallel to a lengthwise direction of the rib.

7. The test method of claim 1, wherein the step of preparing includes the step of
preparing the test specimen having a strip material joined to a remainder of the rib and extending parallel to a lengthwise direction of the rib, wherein the strip material is different from a rib material that forms a remainder of the rib.

8. The test method of claim 1, wherein the step of preparing includes the step of
preparing the test specimen having a mass of the base at least 25 times larger than a mass of the rib.

9. The test method of claim 1, wherein the step of preparing includes the step of
preparing the test specimen having a width of the base at least 5 times larger than a width of the rib.

10. The test method of claim 1, wherein the step of preparing includes the step of
preparing the test specimen having a height of the base at least 3 times larger than a height of the rib.

11. The test method of claim 1, wherein the step of thermally cycling includes the step of
maintaining the rib in compression while the rib is at the higher rib temperature.

12. The test method of claim 1, wherein the step of thermally cycling includes the step of
maintaining the base at a lower temperature than the rib when the rib is heated toward the higher rib temperature.

13. The test method of claim 1, wherein the step of thermally cycling includes the step of
thermally cycling the test specimen in a plurality of test cycles.

14. The test method of claim 1, wherein the step of thermally cycling includes the step of
thermally cycling the test specimen by general heating.

15. The test method of claim 1, wherein the step of thermally cycling includes the step of
thermally cycling the test specimen by local heating of the rib.

16. The test method of claim 1, wherein the step of thermally cycling includes the step of
heating the rib to the higher rib temperature, holding the rib at the higher rib temperature for a period of time, and thereafter cooling the rib to a lower rib temperature.

17. The test method of claim 1, including an additional step, prior to the step of thermally cycling, of
insulating at least a portion of the base.

18. The test method of claim 1, wherein the step of evaluating includes the step of
evaluating the test specimen optically for a presence of fatigue cracks in the rib.

19. A test method for testing the thermal mechanical fatigue performance of a test material, the test method comprising the steps of:
preparing a test specimen of the test material, wherein the test specimen comprises
a base, and
a rib extending outwardly from the base, wherein the rib includes a slot therein, so that the rib is supported from the base at a first end of the rib and at a second end of the rib, but does not contact the base in a central portion of the rib;
thermally cycling the test specimen in at least one test cycle, wherein in each test cycle the rib is heated to a higher rib temperature and thereafter cooled to a lower rib temperature, and wherein the rib is maintained in compression while the rib is heated toward the higher rib temperature; and
evaluating the test specimen for thermal mechanical fatigue damage.

20. The test method of claim 19, wherein the step of preparing includes the step of
preparing the test specimen of a nickel-base superalloy test material.

21. The test method of claim 19, wherein the step of preparing includes the step of
preparing the test specimen having a mass of the base at least 25 times larger than a mass of the rib.

22. The test method of claim 19, including an additional step, prior to the step of thermally cycling, of
insulating at least a portion of the base.

23. The test method of claim 19, wherein the step of thermally cycling includes the step of
maintaining the base at a lower temperature than the rib when the rib is at the higher rib temperature.

24. The test method of claim 19, wherein the step of thermally cycling includes the step of
thermally cycling the test specimen in a plurality of test cycles.

25. The test method of claim 1, wherein the step of thermally cycling includes the step of
thermally cycling without the use of force-applying machinery.

* * * * *